(12) United States Patent
Kelemen et al.

(10) Patent No.: US 7,892,536 B2
(45) Date of Patent: Feb. 22, 2011

(54) STORAGE-STABLE GLUCOSE OXIDASE

(75) Inventors: Bradley R. Kelemen, Menlo Park, CA (US); Suzanne E. Lantz, San Carlos, CA (US)

(73) Assignee: Daniso US Inc., Palo Alto, CA (US)

( * ) Notice: Subject to any disclaimer, the term of this patent is extended or adjusted under 35 U.S.C. 154(b) by 36 days.

(21) Appl. No.: 11/959,342

(22) Filed: Dec. 18, 2007

(65) Prior Publication Data

US 2008/0152638 A1 Jun. 26, 2008

Related U.S. Application Data

(60) Provisional application No. 60/875,968, filed on Dec. 20, 2006.

(51) Int. Cl.
*C12N 9/96* (2006.01)
*A61K 38/44* (2006.01)

(52) U.S. Cl. ...................... 424/94.3; 435/188
(58) Field of Classification Search ........................ None
See application file for complete search history.

(56) References Cited

U.S. PATENT DOCUMENTS

| | | | | |
|---|---|---|---|---|
| 4,537,764 | A | | 8/1985 | Pellico et al. |
| 4,576,817 | A | * | 3/1986 | Montgomery et al. ...... 424/94.4 |
| 5,262,151 | A | | 11/1993 | Montgomery |
| 5,266,688 | A | | 11/1993 | Rosenberg |
| 2002/0106725 | A1 | | 8/2002 | Stougaard et al. |
| 2004/0048763 | A1* | | 3/2004 | Busch et al. ................. 510/302 |
| 2004/0137202 | A1* | | 7/2004 | Hamilton et al. ............. 428/174 |
| 2005/0282261 | A1* | | 12/2005 | Sauter et al. ................. 435/183 |
| 2007/0128129 | A1* | | 6/2007 | Stehr et al. .................... 424/50 |

FOREIGN PATENT DOCUMENTS

| EP | 0379556 B1 | 1/1998 |
|---|---|---|
| JP | 6284886 | 10/1994 |
| WO | WO98/20136 A1 | 5/1998 |
| WO | WO99/16472 A1 | 4/1999 |
| WO | WO2004/078773 A1 | 9/2004 |

OTHER PUBLICATIONS

Bhatti, H.N. et al., "Purification and Thermodynamic Characterization of Glucose Oxidase from a Newly Isolated Strain of *Asperigullus niger*", *Canadian Journal of Microbiology*, 52(6):519-524, 2006.
Cioci, "Catalytic Activity of *Aspergillus niger* Glucose Oxidase in Water-Polyol Mixtures", *Catalysis Letter*, 35(3-4):395-405, 1995.
Cioco, F. et al., "Effect of Polyols and Sugars on Heat-Induced Flavin Dissociation in Glucose Oxidase", *Biochemistry and Molecular Biology International*, 34(4):705-712, 1994.
Gouda, M.D. et al., "Stability Studies on Immobilized Glucose Oxidase Using an Amperonmetric Biosensor—Effect of Protein Based Stabilizing Agents", *Electroanalysis*, 13(10):849-855, 2001.
Gouda, M.D. et al., "Thermal Inactivation of Glucose Oxidase", *The Journal of Biological Chemistry*, 278(27):24324-24333, 2003.
Haouz, A. et al., "Involvement of Protein Dynamics in Enzyme Stability—The Case of Glucose Oxidase", *FEBS Letters*, 506(3):216-220, 2001.
Kalisz, H.M. et al., "Crystallization and Preliminary X-Ray Diffraction Studies of Deglycosylated Glucose Oxidase from *Aspergillus niger*", *J. Mol. Biol.*, 213(2):207-9, 1990.
O'Malley, J.J. et al., "Thermal Stability of Glucose Oxidase and its Admixtures with Synthetic Polymers", *Biotechnology and Bioengineering*, 15(5):917-925, 1973.
Ye, W.N. et al., "Influence of additives on Thermostability of Glucose Oxidase", *Enzyme Microb. Technol.*, 10(8):498-502, 1988.
Toyobo Enzymes Diagnostic Reagent Grade, "Glucose Oxidase from *Asperigllus sp.*", www.toyobo.com, code GLO-201.

* cited by examiner

*Primary Examiner*—Lisa J Hobbs

(57) ABSTRACT

The present invention provides methods and compositions comprising at least one glucose oxidase enzyme, wherein the glucose oxidase has improved storage stability. In some preferred embodiments, the glucose oxidase enzyme is stable after exposure to elevated temperatures. In some alternative preferred embodiments, the glucose oxidase has improved storage stability in liquid formulations. In some particularly preferred embodiments, the present invention provides methods and compositions comprising glucose oxidase(s) obtained from *Aspergillus* sp. In some more particularly preferred embodiments, the glucose oxidase is obtained from *A. niger*. The present invention finds use in applications involving cleaning, including personal care applications.

13 Claims, 6 Drawing Sheets

Percent remaining activity after 10 weeks storage at 40 °C

Percent remaining activity after 10 weeks storage at 40 °C

US 7,892,536 B2

STORAGE-STABLE GLUCOSE OXIDASE

This application claims priority to U.S. Provisional Application Ser. No. 60/875,968, filed on Dec. 20, 2006, and to PCT Application Serial No. PCT/US07/15672 and U.S. application Ser. No. 11/825,229, both filed on Jul. 6, 2007, which in turn both claim priority to U.S. Provisional Application Ser. No. 60/818,824, filed on Jul. 6, 2006.

FIELD OF THE INVENTION

The present invention provides methods and compositions comprising at least one glucose oxidase enzyme, wherein the glucose oxidase has improved storage stability. In some preferred embodiments, the glucose oxidase enzyme is stable after exposure to elevated temperatures. In some alternative preferred embodiments, the glucose oxidase has improved storage stability in liquid formulations. In some particularly preferred embodiments, the present invention provides methods and compositions comprising glucose oxidase(s) obtained from *Aspergillus* sp. In some more particularly preferred embodiments, the glucose oxidase is obtained from *A. niger*. The present invention finds use in applications involving cleaning. In some particularly preferred embodiments, the present invention finds use in personal care products and applications.

BACKGROUND OF THE INVENTION

Glucose oxidases (E.C. 1.1.3.4) are enzymes that catalyze the oxidation of glucose with oxygen, such that D-gluconic acid and hydrogen peroxide are formed. These enzymes have numerous industrial uses, including but not limited to the desugaring of eggs, and the removal of oxygen from beverages, as well as in moist food products, flavors, and hermetically-sealed food packages. These enzymes are also used in the detection and elimination of glucose in industrial solutions and body fluids (e.g., blood and urine).

However, these enzymes have been found to be unstable under various conditions. Thus, although the enzymes are used in various industries and in numerous products, there remains a need in the art for glucose oxidase enzymes that are stable under conditions common in these industries. Indeed, most reports of methods for stabilizing the enzyme involve immobilized glucose oxidase used in biosensors. Thus, there remains a need for storage-stable glucose oxidases for use in other industries.

SUMMARY OF THE INVENTION

The present invention provides methods and compositions comprising at least one glucose oxidase enzyme, wherein the glucose oxidase has improved storage stability. In some preferred embodiments, the glucose oxidase enzyme is stable after exposure to elevated temperatures. In some alternative preferred embodiments, the glucose oxidase has improved storage stability in liquid formulations. In some particularly preferred embodiments, the present invention provides methods and compositions comprising glucose oxidase(s) obtained from *Aspergillus* sp. In some more particularly preferred embodiments, the glucose oxidase is obtained from *A. niger*. The present invention finds use in applications involving cleaning.

The present invention provides compositions comprising glucose oxidase and at least one or two storage stability enhancing compounds.

In some embodiments, the invention provides compositions comprising glucose oxidase and at least one or two storage stability enhancing compounds wherein the at least one or two storage stability enhancing compounds is chosen from gluconate, metabisulfite, ascorbate, glucose, and tetra potassium pyrophosphate.

In some embodiments, the invention provides compositions comprising glucose oxidase and at least one or two storage stability enhancing compounds, wherein the storage stability enhancing compounds comprises a solution of 18.5% sodium chloride, 1.3% monosodium phosphate, dihydrate, and 2.5% trisodium citrate, dihydrate and at least one further storage enhancing compound selected from tetra potassium pyrophosphate, ammonium sulfate, ammonium tartrate, and tetra sodium pyrophosphate.

In some embodiments, the invention provides compositions comprising glucose oxidase and at least one or two storage stability enhancing compounds, wherein the compositions retain at least about 15% of its initial activity after about 10 weeks of storage at about 40° C.

In other embodiments, the invention provides compositions comprising glucose oxidase and at least one or two storage stability enhancing compounds, wherein the compositions retain at least about 30% of its initial activity after about 10 weeks of storage at about 40° C.

In other embodiments, the invention provides compositions comprising glucose oxidase and at least one or two storage stability enhancing compounds, wherein the compositions retain at least about 50% of its initial activity after about 10 weeks of storage at about 40° C.

In yet other embodiments, the invention provides compositions comprising glucose oxidase and at least one or two storage stability enhancing compounds, wherein the compositions retain at least about 70% of its initial activity after about 10 weeks of storage at about 40° C.

The present invention further provides compositions comprising glucose oxidase and at least one or two storage stability enhancing compounds, wherein the compositions are personal care compositions.

In some embodiments, the present invention provides compositions comprising glucose oxidase and at least one or two storage stability enhancing compounds, wherein the compositions are stable after storage at a pH range of about 5.0 to about 7.

In some embodiments, the invention provides compositions comprising glucose oxidase and at least one or two storage stability enhancing compounds, wherein the compositions are stable after storage at about pH 7.

In yet additional embodiments, the present invention provides compositions comprising glucose oxidase and at least one or two storage stability enhancing compounds, wherein the compositions are stable after storage at a temperature ranging from about 4° C. to about 50° C.

In some embodiments, the present invention provides compositions comprising glucose oxidase and at least one or two storage stability enhancing compounds, wherein the compositions are stable after storage at a temperature ranging from less than about 4° C. to about 40° C.

The present invention also provides methods for stabilizing glucose oxidase in a composition comprising: providing glucose oxidase and at least one stability enhancing compound; and combining said glucose oxidase and said at least one stability enhancing compound to produce a stabilized glucose oxidase composition.

In some embodiments, the invention provides methods for stabilizing glucose oxidase in a composition comprising: providing glucose oxidase and at least one stability enhancing compound; and combining said glucose oxidase and said at least one stability enhancing compound to produce a stabilized glucose oxidase composition, wherein the at least one storage stability enhancing compound is selected from gluconate, metabisulfite, ascorbate, and glucose.

In additional embodiments, the invention provides methods for stabilizing glucose oxidase in a composition comprising: providing glucose oxidase and at least one stability enhancing compound; and combining said glucose oxidase and said at least one stability enhancing compound to produce a stabilized glucose oxidase composition, wherein the composition comprises at least two storage stability enhancing compounds, and wherein at least one of said storage stability enhancing compounds is selected from gluconate, metabisulfite, ascorbate, glucose, and tetra potassium pyrophosphate.

In some embodiments, the invention provides methods for stabilizing glucose oxidase in a composition comprising: providing glucose oxidase and at least one stability enhancing compound; and combining said glucose oxidase and said at least one stability enhancing compound to produce a stabilized glucose oxidase composition, wherein the composition comprises a solution of 18.5% sodium chloride, 1.3% monosodium phosphate, dihydrate, and 2.5% trisodium citrate, dihydrate, and at least one additional storage stability enhancing compound selected from tetra potassium pyrophosphate, ammonium sulfate, ammonium tartrate, and tetra sodium pyrophosphate.

In some embodiments, the invention provides methods for stabilizing glucose oxidase in a composition comprising: providing glucose oxidase and at least one stability enhancing compound; and combining said glucose oxidase and said at least one stability enhancing compound to produce a stabilized glucose oxidase composition, wherein the composition is stable for about 10 weeks at about 40° C.

In some embodiments, the invention provides methods for stabilizing glucose oxidase in a composition comprising: providing glucose oxidase and at least one stability enhancing compound; and combining said glucose oxidase and said at least one stability enhancing compound to produce a stabilized glucose oxidase composition, wherein the composition is a personal care composition.

DESCRIPTION OF THE INVENTION

Figure 1:
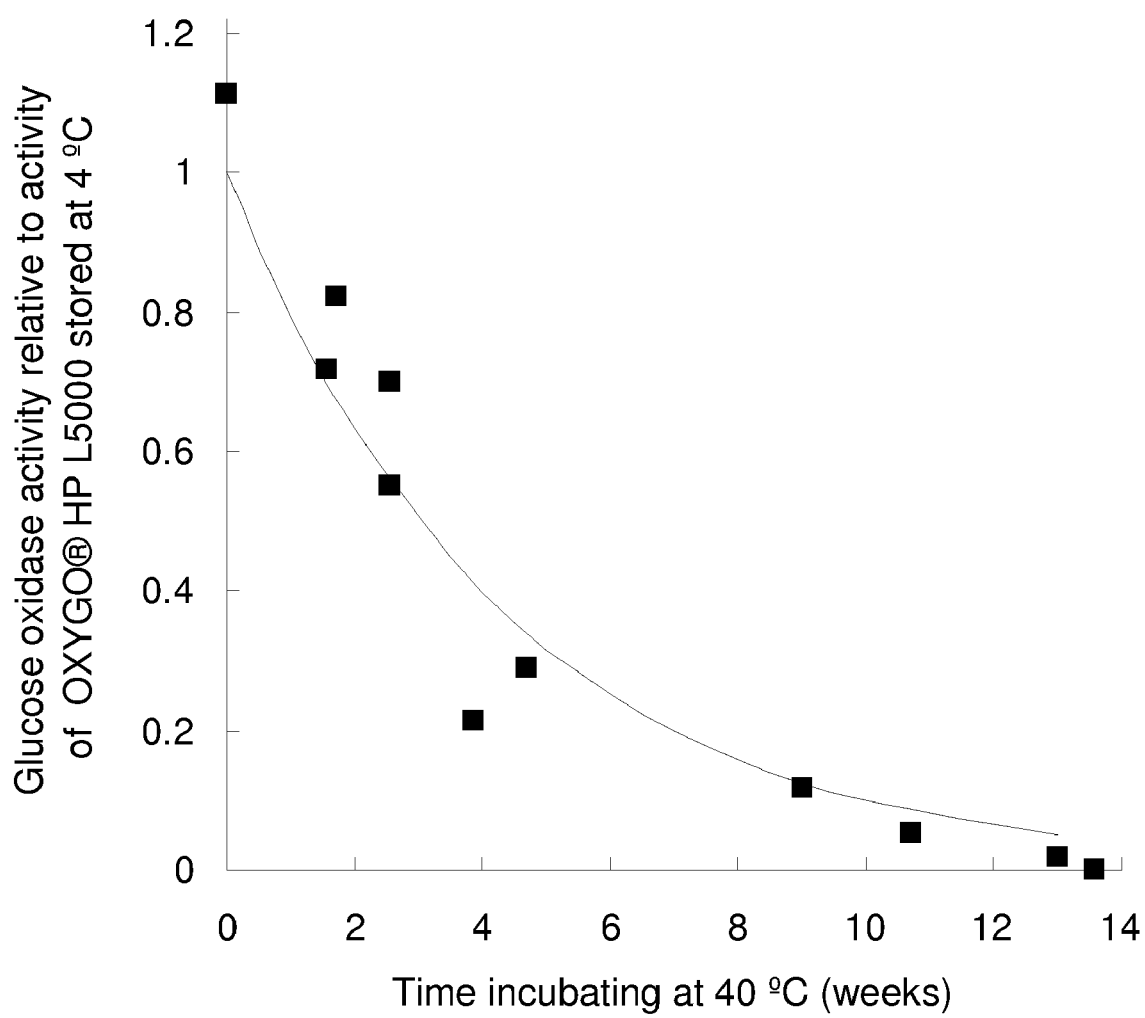
FIG. 1 provides a graph that shows the activity of samples of glucose oxidase in 20 mM citrate, 20 mM phosphate pH 6.0 when stored at 40° C., relative to the activity of OXYGO® HP L5000 stored at 4° C. The solid line represents the values of activity determined from a best fit of the data to equation 1. A value of remaining activity was determined at 10 weeks, in order to facilitate a functional comparison to the stability of other samples.
Figure 2:
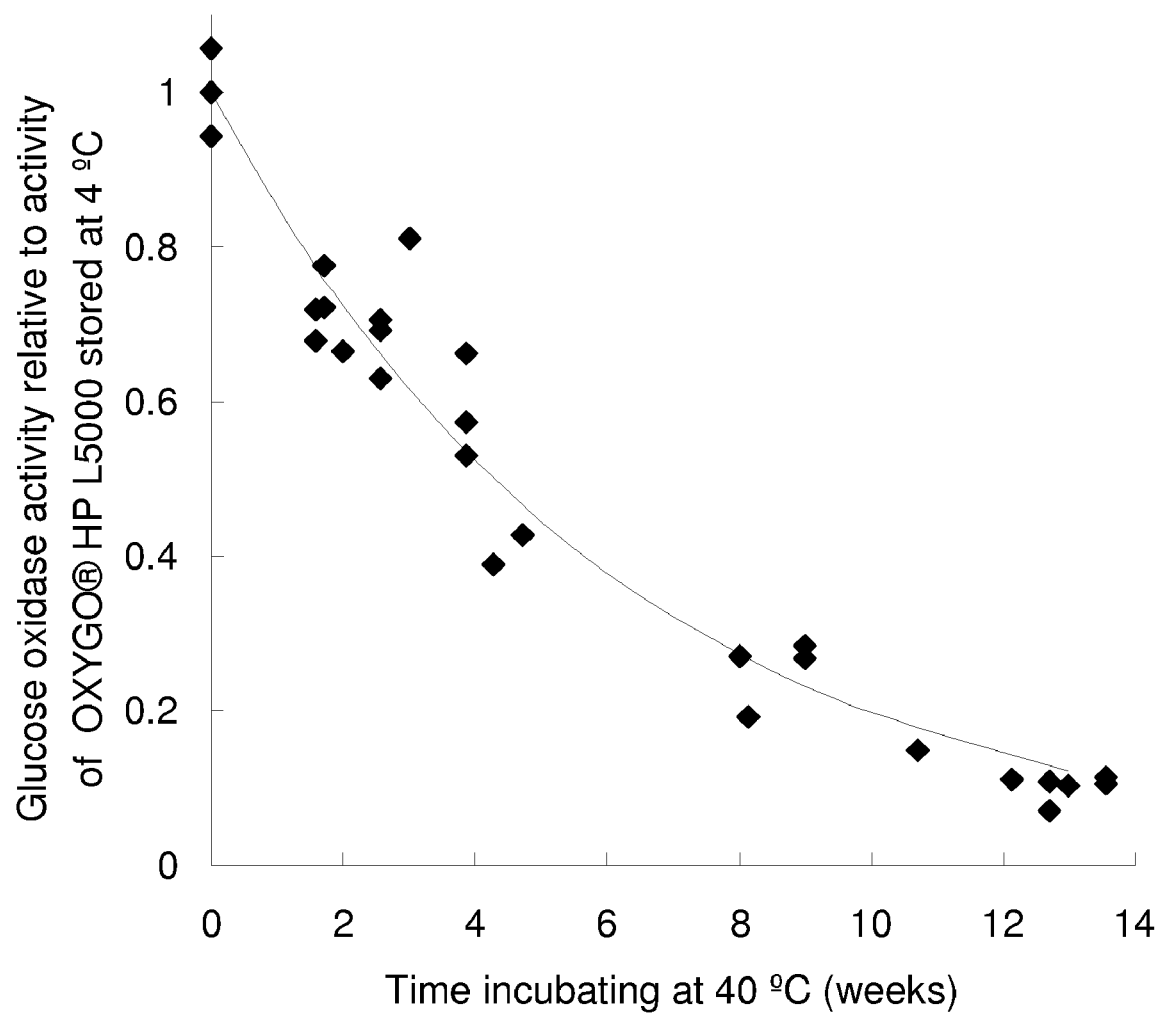
FIG. 2 provides a graph that shows the activity of samples of glucose oxidase formulated in Base A when stored at 40° C., relative to the activity of OXYGO® HP L5000 stored at 4° C. The solid line represents the values of activity determined from a best fit of the data to equation 1. A value of remaining activity was determined at 10 weeks, in order to facilitate a functional comparison to the stability of other samples.
Figure 3:
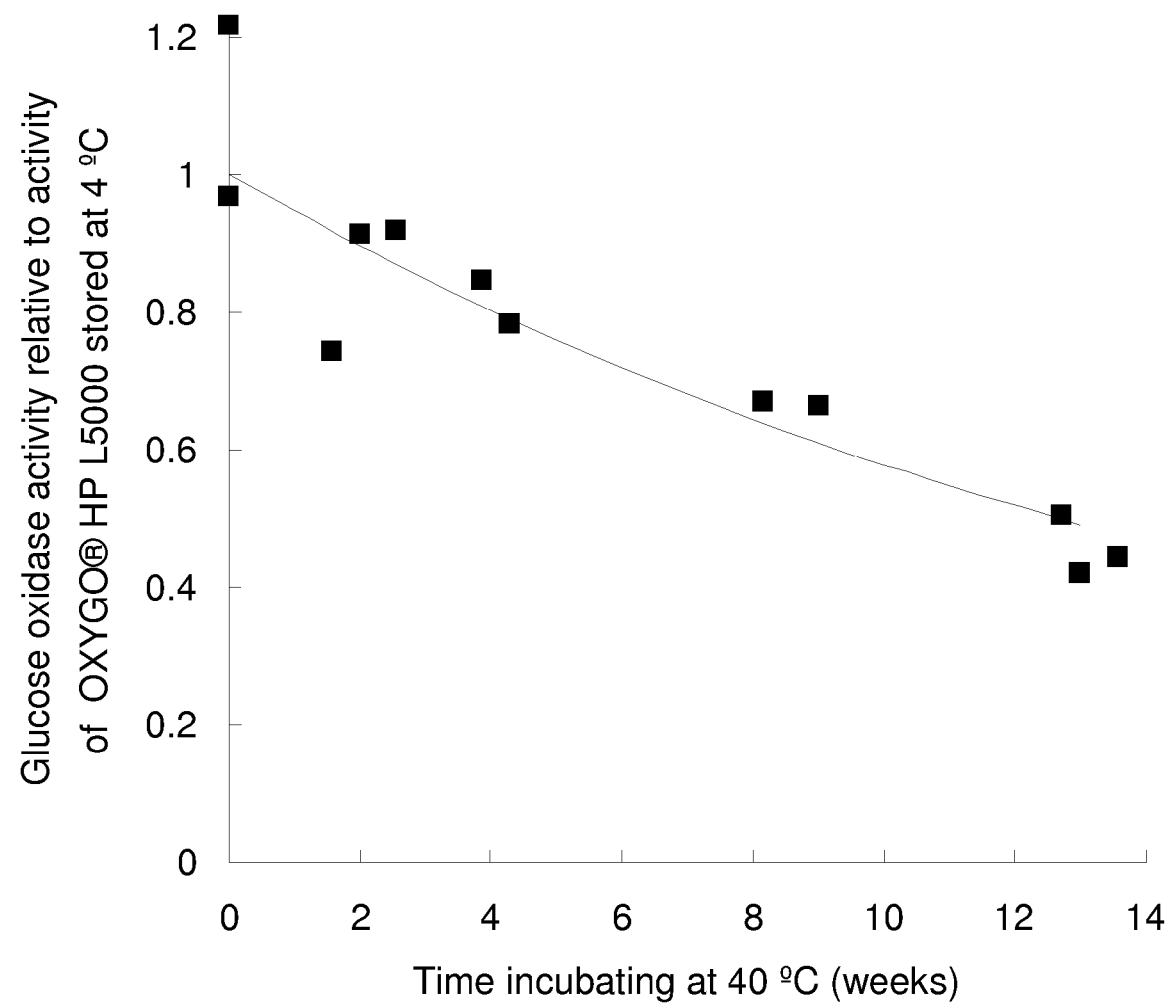
FIG. 3 provides a graph that shows the activity of samples of glucose oxidase formulated with 2.4% tetrapotassium pyrophosphate and Base A when stored at 40° C., relative to the activity of OXYGO® HP L5000 stored at 4° C. The solid line represents the values of activity determined from a best fit of the data to equation 1. A value of remaining activity was determined at 10 weeks to facilitate a functional comparison to the stability of other samples.
Figure 4:
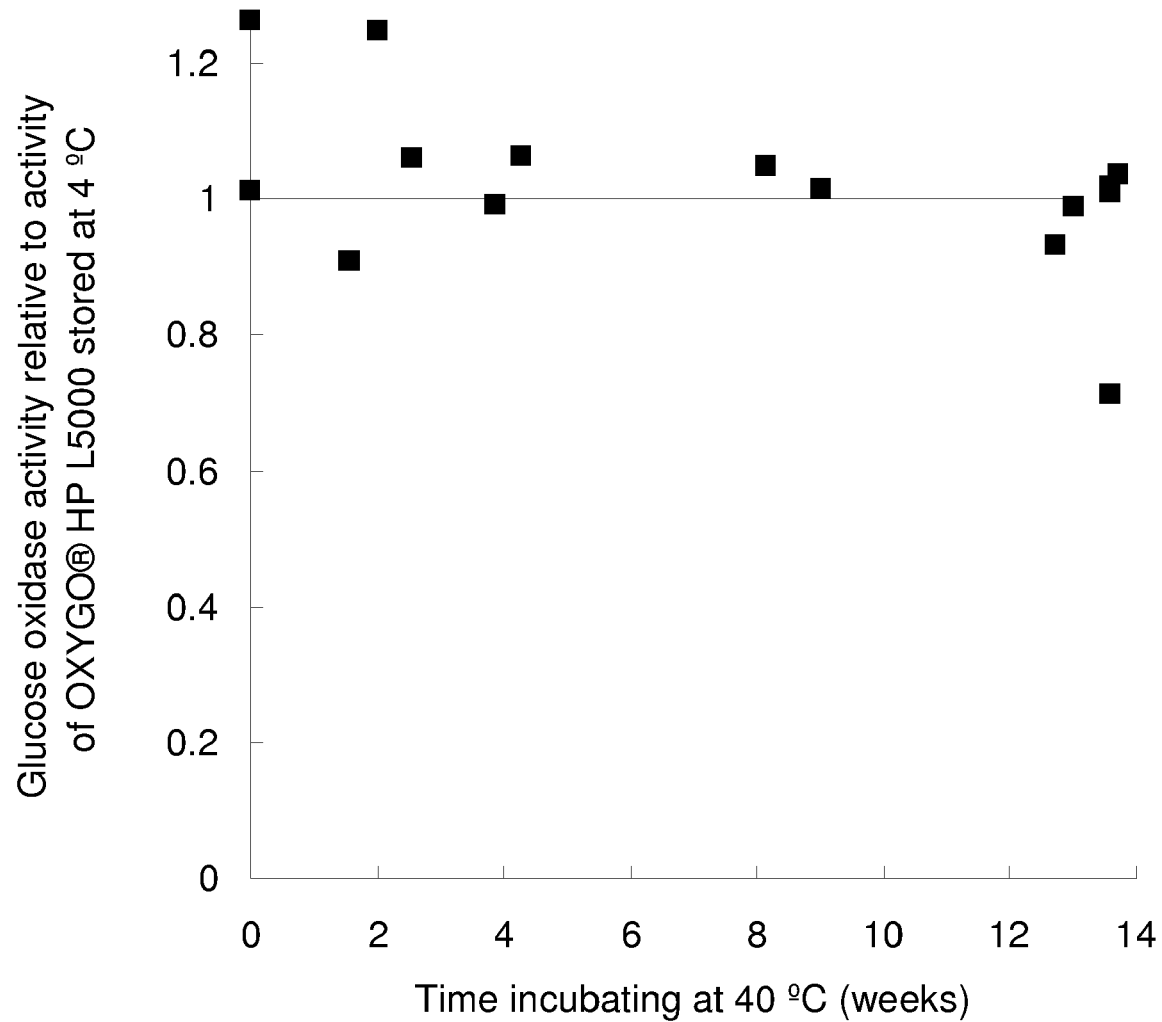
FIG. 4 provides a graph that shows the activity of samples of glucose oxidase formulated in 33% sodium gluconate when stored at 40° C., relative to the activity of OXYGO® HP L5000 stored at 4° C. The solid line represents the values of activity determined from a best fit of the data to equation 1. A value of remaining activity was determined at 10 weeks, in order to facilitate a functional comparison to the stability of other samples.

The present invention provides methods and compositions comprising at least one glucose oxidase enzyme, wherein the glucose oxidase has improved storage stability. In some preferred embodiments, the glucose oxidase enzyme is stable after exposure to elevated temperatures. In some alternative preferred embodiments, the glucose oxidase has improved storage stability in liquid formulations. In some particularly preferred embodiments, the present invention provides methods and compositions comprising glucose oxidase(s) obtained from *Aspergillus* sp. In some more particularly preferred embodiments, the glucose oxidase is obtained from *A. niger*. The present invention finds use in applications involving cleaning. In some particularly preferred embodiments, the present invention finds use in personal care products and applications.

Unless otherwise indicated, the practice of the present invention involves conventional techniques commonly used in molecular biology, microbiology, protein purification, formulation development, etc., which are within the skill of the art. All patents, patent applications, articles and publications mentioned herein, both supra and infra, are hereby expressly incorporated herein by reference.

Furthermore, the headings provided herein are not limitations of the various aspects or embodiments of the invention which can be had by reference to the specification as a whole. Accordingly, the terms defined immediately below are more fully defined by reference to the specification as a whole. Nonetheless, in order to facilitate understanding of the invention, a number of terms are defined below.

DEFINITIONS

Unless defined otherwise herein, all technical and scientific terms used herein have the same meaning as commonly understood by one of ordinary skill in the art to which this invention pertains. For example, Singleton and Sainsbury, *Dictionary of Microbiology and Molecular Biology*, 2d Ed., John Wiley and Sons, NY (1994); and Hale and Marham, *The Harper Collins Dictionary of Biology*, Harper Perennial, N.Y. (1991) provide those of skill in the art with a general dictionaries of many of the terms used in the invention. Although any methods and materials similar or equivalent to those described herein find use in the practice of the present invention, the preferred methods and materials are described herein. Accordingly, the terms defined immediately below are more fully described by reference to the Specification as a whole. Also, as used herein, the singular terms "a," "an," and "the" include the plural reference unless the context clearly indicates otherwise. Unless otherwise indicated, nucleic acids are written left to right in 5' to 3' orientation; amino acid sequences are written left to right in amino to carboxy orientation, respectively. It is to be understood that this invention is not limited to the particular methodology, protocols, and reagents described, as these may vary, depending upon the context they are used by those of skill in the art.

It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

All documents cited are, in relevant part, incorporated herein by reference; the citation of any document is not to be construed as an admission that it is prior art with respect to the present invention.

As used herein, "OXYGO®" and "OXYGO® HP L5000" refer to the product containing purified glucose oxidase commercially available from Genencor under the name "OXYGO® HP L5000." This enzyme is a highly purified *A. niger* glucose oxidase that is derived from a genetically modified strain of *A. niger*.

As used herein, the term "a unit of glucose oxidase activity" refers to the activity of glucose oxidase expressed in titrimetic units ("Titr. U" or "U") per ml. One Titrimetric Unit will oxidize 3.0 mg glucose to gluconic acid in 15 minutes, under assay conditions of pH 5.1, at 35° C. The value obtained for OXYGO® HP L5000 was used as the calibration standard for the assay provided below.

As used herein, the term "stability enhancing compound" refers to a compound that imparts stability and/or improved stability to the glucose oxidase in a composition. In particularly preferred embodiments, the term is used in reference to compounds that provide improved stability at about 40° C. for about 10 weeks. However, it is not intended that the present invention be limited to these conditions, as the term is intended to encompass any compound that provides improved stability to glucose oxidase as compared to glucose oxidase in the absence of the compound.

As used herein, "cosmetic composition" refers to compositions that find use in the cosmetics. The Food Drug and Cosmetic Act (FD&C Act) definition is used herein. Thus, cosmetics are defined by their intended use, as articles intended to be rubbed, poured, sprinkled, or sprayed on, introduced into, or otherwise applied to the human body for cleansing, beautifying, promoting attractiveness, or altering appearance. These compositions provide non-therapeutic benefits and are not regulated as pharmaceuticals. However, in some situations, cosmetic compositions are incorporated into pharmaceutical compositions to provide cosmetic benefits (e.g., products that treat skin or hair diseases, but also contain cosmetic compositions for their coloring or other benefits). Also, it is intended that the present invention encompass the use of cosmetics on animals other than humans.

As used herein, the term "personal care composition" and "personal care product" refer to a composition and/or product for application to the skin, hair, nails, oral cavity and related membranes for the purposes of improving, cleaning, beautifying, treating, and/or caring for these surfaces and membranes. In some particularly preferred embodiments, these products are utilized on humans, while in other embodiments, these products find use with non-human animals (e.g., in veterinary applications).

As used herein, "cleaning compositions" and "cleaning formulations," unless otherwise indicated, refer to compositions that find use in the removal of undesired compounds from items to be cleaned, such as fabric, dishes, contact lenses, other solid substrates. The term encompasses any materials/compounds selected for the particular type of cleaning composition desired and the form of the product (e.g., liquid, gel, granule, or spray composition), as long as the composition is compatible with the glucose oxidase and other enzyme(s) used in the composition.

As used herein, the term "compatible," means that the cleaning composition materials do not reduce the enzymatic activity of the glucose oxidase to such an extent that the glucose oxidase is not effective as desired during normal use situations. Specific cleaning composition materials are exemplified in detail hereinafter.

As used herein, "effective amount of enzyme" refers to the quantity of enzyme necessary to achieve the enzymatic activity required in the specific application (e.g., personal care product, cleaning composition, etc.). Such effective amounts are readily ascertained by one of ordinary skill in the art and are based on many factors, such as the particular enzyme variant used, the cleaning application, the specific composition of the cleaning composition, and whether a liquid or dry (e.g., granular, bar) composition is required, and the like.

As used herein, "non-fabric cleaning compositions" encompass hard surface cleaning compositions, dishwashing compositions, personal care cleaning compositions and compositions suitable for use in the pulp and paper industry.

As used herein, the term "enzymatic conversion" refers to the modification of a substrate to an intermediate or the modification of an intermediate to an end-product by contacting the substrate or intermediate with an enzyme. In some embodiments, contact is made by directly exposing the substrate or intermediate to the appropriate enzyme. In other embodiments, contacting comprises exposing the substrate or intermediate to an organism that expresses and/or excretes the enzyme, and/or metabolizes the desired substrate and/or intermediate to the desired intermediate and/or end-product, respectively.

As used herein, the phrase, "stability to proteolysis" refers to the ability of a protein (e.g., an enzyme) to withstand proteolysis. It is not intended that the term be limited to the use of any particular glucose oxidase to assess the stability of a protein.

As used herein, "oxidative stability" refers to the ability of a protein to function after incubation under oxidative conditions.

As used herein, "pH stability" refers to the ability of a protein to function after incubation at a particular pH. In some preferred embodiments, the glucose oxidases of the present invention function after exposure to pHs in the range of about 5 to about 7. However, it is not intended that the present invention be limited to any specific pH stability level nor pH range.

As used herein, "thermal stability" refers to the ability of a protein to function after incubation at a particular temperature. In some preferred embodiments, the glucose oxidases of the present invention are able to function after exposure to temperatures ranging from about 4° C. to about 50° C. In some particularly preferred embodiments, the glucose oxidases of the present invention are able to function after exposure to temperatures ranging from less than about 4° C. to about 40° C. However, it is not intended that the present invention be limited to any temperature stability level nor temperature range.

As used herein, the term "chemical stability" refers to the stability of a protein (e.g., an enzyme) after exposure to chemicals that adversely affect its activity. It is not intended that the present invention be limited to any particular chemical stability level nor range of chemical stability.

As used herein, "surface property" is used in reference to an electrostatic charge, as well as properties such as the hydrophobicity and/or hydrophilicity exhibited by the surface of a protein.

As used herein, the terms "purified" and "isolated" refer to the removal of contaminants from a sample. For example, glucose oxidase are purified by removal of contaminating proteins and other compounds within a solution or preparation that are not glucose oxidase. In some embodiments, recombinant glucose oxidase are expressed in bacterial or fungal host cells and these recombinant glucose oxidases are purified by the removal of other host cell constituents; the percent of recombinant glucose oxidase polypeptides is thereby increased in the sample. In particularly preferred embodiments, the glucose oxidase of the present invention is substantially purified to a level of at least about 99% of the protein component, as determined by SDS-PAGE or other standard methods known in the art. In some alternative preferred embodiments, the glucose oxidase of the present invention comprises at least about 99% of the glucose oxidase component of the compositions. In yet alternative embodiments, the glucose oxidase is present in a range of about at least 90-95% of the total protein. However, it is not intended that the present invention be limited to glucose oxidases of a specific purity level. For example, in some embodiments, the purity level needed for use is in the range of from about 75% to about 80%. Thus, in some embodiments, the glucose oxidases of the present invention find use at purity levels that are fairly low. In some alternative embodiments, the glucose oxidases are "purified" in that the catalase concentration in the composition is sufficiently low that it does not destroy the product of the glucose oxidase reaction (i.e., $H_2O_2$).

As used herein, "protein of interest," refers to a protein (e.g., an enzyme or "enzyme of interest") which is being analyzed, identified and/or modified. Naturally-occurring, as well as recombinant proteins find use in the present invention.

As used herein, "protein" refers to any composition comprised of amino acids and recognized as a protein by those of skill in the art. The terms "protein," "peptide" and "polypeptide" are used interchangeably herein. Wherein a peptide is a portion of a protein, those skilled in the art understand the use of the term in context.

As used herein, functionally and/or structurally similar proteins are considered to be "related proteins." In some embodiments, these proteins are derived from a different genus and/or species, including differences between classes of organisms (e.g., a bacterial protein and a fungal protein). In some embodiments, these proteins are derived from a different genus and/or species, including differences between classes of organisms (e.g., a bacterial enzyme and a fungal enzyme). In additional embodiments, related proteins are provided from the same species. Indeed, it is not intended that the present invention be limited to related proteins from any particular source(s). In addition, the term "related proteins" encompasses tertiary structural homologs and primary sequence homologs (e.g., the glucose oxidase of the present invention). In further embodiments, the term encompasses proteins that are immunologically cross-reactive.

DETAILED DESCRIPTION OF THE PRESENT INVENTION

The present invention provides methods and compositions comprising at least one glucose oxidase enzyme, wherein the glucose oxidase has improved storage stability. In some preferred embodiments, the glucose oxidase enzyme is stable after exposure to elevated temperatures. In some alternative preferred embodiments, the glucose oxidase has improved storage stability in liquid formulations. In some particularly preferred embodiments, the present invention provides methods and compositions comprising glucose oxidase(s) obtained from *Aspergillus* sp. In some more particularly preferred embodiments, the glucose oxidase is obtained from *A. niger*. The present invention finds use in applications involving cleaning.

In some embodiments, the use of glucose oxidase in some personal care products as an active ingredient requires the demonstration that the enzyme is stable in storage at elevated temperatures (e.g., about 40° C.) for an extended period of time. The Food and Drug Administration (FDA) sets requirements for product shelf-life based on the stability of active ingredients, as determined by stability tests (See e.g., 21 C.F.R. 211). Thus, in some particularly preferred embodiments, the storage stability requirements for the stability of an active ingredient set forth by the FDA are met. However, it is not intended that the present invention be limited to any particular storage temperature.

The loss of glucose oxidase activity can result from various insults to the enzyme. However, during the development of the present invention, it was determined that the addition of reducing agents (e.g., metabisulfite, beta-mercaptoethanol, and ascorbate) improved the stability of glucose oxidase, along with the addition of catalase. In some embodiments, it is contemplated that a synergistic benefit be provided by the combination of reducing agents and catalase provides a synergistic effect. The addition of high concentrations of gluconate, was also found to stabilize glucose oxidase activity. In addition, other polyalcohols also had a stabilizing effect, including but not limited to combinations of polyethylene glycol, sorbitol, glycerol, and catalase (See e.g., Table 1, below).

In preferred embodiments, at least one polyalcohol is used to stabilize the glucose oxidase of the present invention. Examples of polyalcohols that find use in the present invention include, but are not limited to polyalkylene oxides (PAO), polyalkylene glycols (PAG), polymethylene glycols, polyethylene glycols (PEG), methoxypolyethylene glycols (mPEG), polypropylene glycols, polyvinyl alcohol (PVA), polyethylene-co-maleic acid anhydride, polystyrene-co-malic acid anhydride, dextrans (e.g., carboxymethyl-dextrans), celluloses (e.g., methylcellulose, carboxymethylcellulose, ethylcellulose, hydroxyethylcellulose, carboxyethylcellulose, and hydroxypropylcellulose), hydrolysates of chitosan, starches (e.g., hydroxyethyl starches and hydroxy propyl starches), glycogen, agaroses and derivates thereof, guar gum, pullulan, inulin, xanthan gum, carrageenan, pectinc, alginic acid hydrolysates, biopolymers, sorbitol, glucose, mannose, galactose, arabinose, gulose, xylose, threose, sorbose, fructose, glycerol, maltose, cellobiose, sucrose, amylase, amylopectin, and mono-propylene glycol; gluconates (e.g. sodium gluconate, potassium gluconate).

In some embodiments, the compositions of the present invention comprise at least one polymer and/or a saccharide. Suitable polymers include, but are not limited to polyalkylene oxide (PA), polyalkylene glycol (PAG), and polypropylene glycol.

In some additional embodiments, the compositions of the present invention comprise at least one further ingredient. In some embodiments, the further ingredients are selected from antimicrobial agents, pH-regulating agents, dispersing agents, viscosity-regulating agents, and antioxidants.

As used herein, "antimicrobial agents" refers to compounds that kill, inhibit or prevent the growth of microorganisms, including bacteria, fungi, viruses, and parasites. In some embodiments, the antimicrobial agents include chemical agents, including, but not limited to sodium benzoates, potassium sorbate, and parabens. The term also encompasses any suitable antibiotic (i.e., an antimicrobial that is produced by a microorganism, as well as the synthetic analogs of such suitable antibiotics).

As used herein, "dispersing agents" are compounds that help to prevent or delay separation (e.g., precipitation) of dispersed solid substances. Suitable agents include, but are not limited to certain finely divided clays (e.g., kaolin, china clay, bentonite, fuller's earth, etc.), as well as "deflocculating polymers," and amphipathic materials of the anionic polymer type.

As used herein, "pH regulating agents" refer to compounds which when the composition of the invention is brought into contact with an aqueous medium, aid in adjusting and/or maintaining (i.e., buffering) the pH of the medium so as to provide a pH value which is compatible with pH-sensitive components of the composition. Suitable agents include, but are not limited to various anhydrous inorganic and organic salts (e.g., potassium dihydrogen phosphate, sodium hydrogen carbonate, potassium acetate, sodium acetate, and potassium dihydrogen citrate), glycine buffer, and Tris-sodium buffer.

As used herein, "antioxidants" refer to compounds which can protect an oxidation-sensitive component of the composition of some embodiments of the present invention against oxidation (e.g., by atmospheric oxygen). However, in some embodiments, oxidation can also occur from $H_2O_2$ or oxygen radicals generated from $H_2O_2$ by other components of the formulation. Suitable antioxidants include, but are not limited to methionine and lecithins.

During the development of the present invention, low concentrations of chemicals were added to glucose oxidase in Base A and glucose oxidase in Base B (See, below). These chemicals included surfactants, chelating agents, polymers, chaotropic salts, buffers, reducing agents, slow substrates, end products, catalase, and combinations of these agents. In addition, polymers, sugar alcohols, sugars, and sodium gluconate were used as excipients in the formulation of glucose oxidase. Several of these approaches were found to provide stability benefits to the glucose oxidase. Although the glucose oxidase in OXYGO® was used during the development of the present invention, it is not intended that the present invention be limited to this particular glucose oxidase, as the present invention finds use with any glucose oxidase. In addition, it is contemplated that the present invention will find use in stabilizing other enzymes that bind glucose, including, but not limited to glucooligosaccharide oxidase, hexose oxidase, lactose oxidase, and pyranose oxidase. In addition, it is contemplated that the present invention will find use in stabilizing sorbitol oxidase. Indeed, it is not intended that the present invention will be limited to any specific enzyme. In some particularly preferred embodiments, gluconate finds use in stabilizing the active sites of various enzymes, thereby increasing the stability of the enzyme maintained at high temperatures for prolonged time periods. However, it is not intended that the present invention be limited to any particular mechanism of action.

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: ° C. (degrees Centigrade); rpm (revolutions per minute); $H_2O$ (water); HCl (hydrochloric acid); aa (amino acid); bp (base pair); kb (kilobase pair); kD (kilodaltons); gm (grams); μg and ug (micrograms); mg (milligrams); ng (nanograms); μl and ul (microliters); ml (milliliters); mm (millimeters); nm (nanometers); μm and um (micrometer); M (molar); mM (millimolar); μM and uM (micromolar); U (units); V (volts); MW (molecular weight); sec (seconds); min(s) (minute/minutes); hr(s) (hour/hours); $MgCl_2$ (magnesium chloride); NaCl (sodium chloride); $OD_{280}$ (optical density at 280 nm); $OD_{600}$ (optical density at 600 nm); PAGE (polyacrylamide gel electrophoresis); EtOH (ethanol); PBS (phosphate buffered saline [150 mM NaCl, 10 mM sodium phosphate buffer, pH 7.2]); SDS (sodium dodecyl sulfate); Tris (tris(hydroxymethyl)aminomethane); Genencor (Genencor, Palo Alto, Calif.); Molecular Devices (Molecular Devices, Corp., Sunnyvale, Calif.); Amersham (Amersham Life Science, Inc. Arlington Heights, Ill.); Corning (Corning International, Corning, N.Y.); ICN (ICN Pharmaceuticals, Inc., Costa Mesa, Calif.); Pierce (Pierce Biotechnology, Rockford, Ill.); Amicon (Amicon, Inc., Beverly, Mass.); ATCC (American Type Culture Collection, Manassas, Va.); Becton Dickinson (Becton Dickinson Labware, Lincoln Park, N.J.); Perkin-Elmer (Perkin-Elmer, Wellesley, Mass.); Waters (Waters, Inc., Milford, Mass.); Perseptive Biosystems (Perseptive Biosystems, Ramsey, Minn.); Difco (Difco Laboratories, Detroit, Mich.); GIBCO BRL or Gibco BRL (Life Technologies, Inc., Gaithersburg, Md.); Novagen (Novagen, Inc., Madison, Wis.); Novex (Novex, San Diego, Calif.); Sigma (Sigma-Aldrich Chemical Co., St. Louis, Mo.); DuPont Instruments (Asheville, N.Y.); Global Medical Instrumentation or GMI (Global Medical Instrumentation; Ramsey, Minn.); Agilent (Agilent Technologies, Palo Alto, Calif.).

In the following Examples, the *Aspergillus niger* glucose oxidase found in OXYGO® HP L5000 (Genencor) was used. Salts were removed from the enzyme by extensive dialysis against 20 mM phosphate 20 mM citrate buffer pH 6.0. This dialyzed material was then concentrated to approximately 15000 units/ml. Stabilizing components were either added directly to OXYGO® HP L-5000 to a given concentration such that the OXYGO® HP L-5000 was not diluted more than 15% or added to the above dialyzed concentrate of glucose oxidase such that the final enzyme concentration was approximately 5000 units/ml. Samples of these new formulations and the original OXYGO® HP L-5000 (1 ml volume in 1.5 ml microcentrifuge tubes) were placed at 40° C. and incubated for defined periods. A small aliquot (17 μl) of these samples was taken at intervals of approximately one week, two weeks, four weeks, and eight weeks. These aliquots were successively diluted 14641 fold into 100 mM phosphate buffer pH 7.0 with 0.05% TWEEN®-20 and measured immediately for glucose oxidase activity.

Glucose Oxidase Activity Protocol

A reagent mixture was prepared daily, which contained 2.74 mg/ml ABTS (2,2'-azino-bis(3-ethylbenzothiazoline-6-sulfonic acid; Sigma A1888-5g), 100 mM phosphate buffer (pH 7.0), 50 mM glucose, and 2.5 purpurogallin units/ml horseradish peroxidase (Sigma).

Glucose oxidase standards were prepared by diluting OXYGO®HP L5000 from 5000 U/ml to 0.4-0.05 U/ml, with 100 mM phosphate buffer (pH 7.0), and including a buffer blank. Enzyme samples were diluted to an expected concentration within the standard curve range.

Figure 5A:
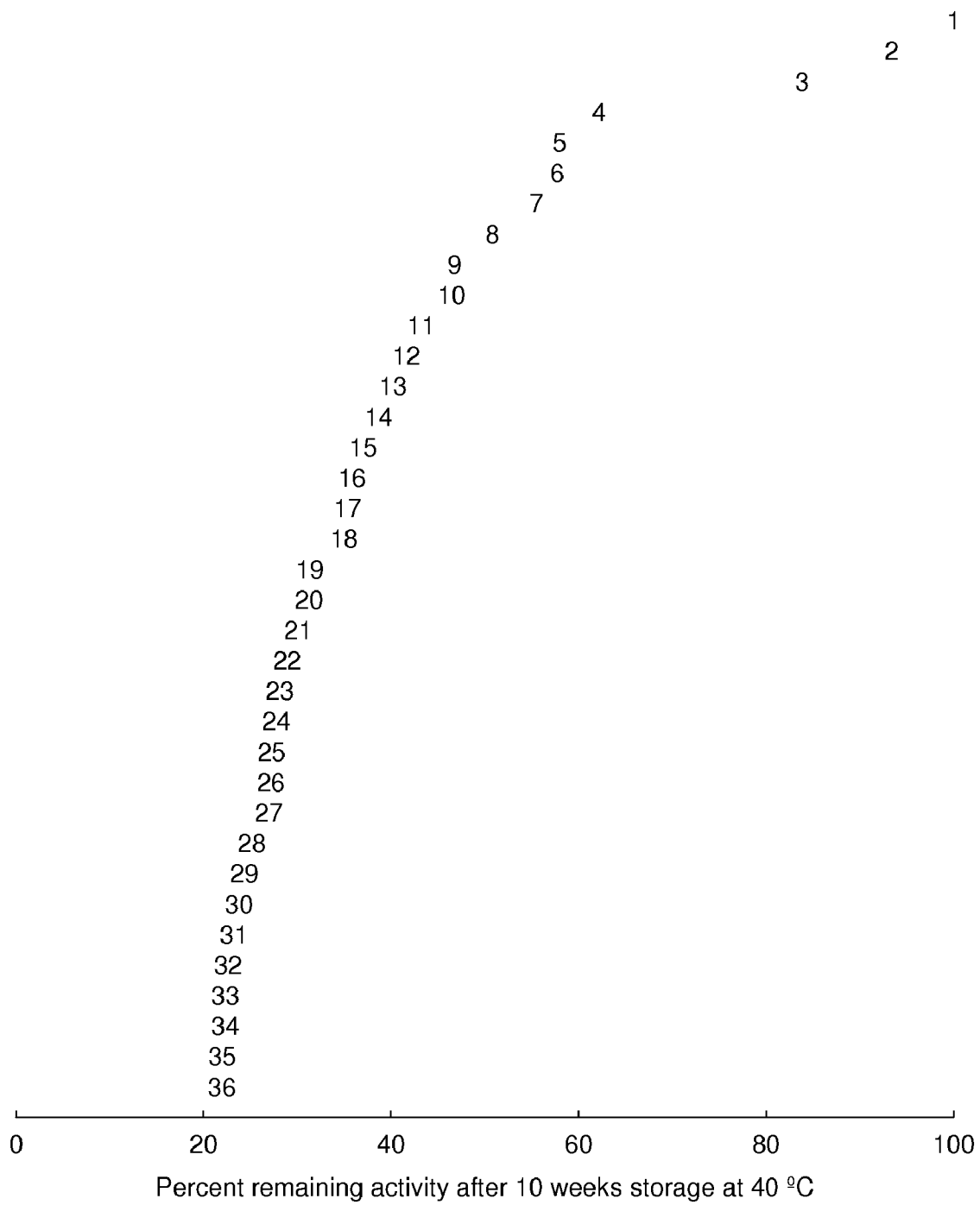
FIG. 5A and FIG. 5B provide graphs that show the values of percent remaining activity after 10 weeks storage at 40° C., calculated from the value of the rate constant, k, determined from non-linear least squares regression analysis fitting to equation 1.
Figure 5B:

A SpectraMax 250 spectrophotometer (Molecular Devices) was set for kinetic analysis, with mixing prior to sampling and reading at 405 nm. For reading, 95 ul of reaction mixture was transferred into clear bottom 96-well microtiter plates (MTP). Then, 5 ul of either the diluted enzyme sample or the glucose oxidase standard were added to the reaction mixture in the MTP. The MTP was then placed into the spectrophotometer and read for 5 minutes, at 30-second intervals, at room temperature. Absorbance data were reduced to the slope of the absorbance change as a function of time. The activity in the sample of each composition was calculated against a linear standard curve of OXYGO® HP L5000 stored at 4° C. (i.e., a condition which has been shown to maintain 100% residual activity). Table 1 provides the compositions of the samples tested. The "Sample Number" corresponds to the numbers in the FIGS. 5A and 5B.

TABLE 1

Compositions Tested

| Sample Number | Composition | Fraction Remaining After 10 weeks Storage at 40° C. |
|---|---|---|
| 1 | 33% sodium gluconate | 100.0 |
| 2 | 20% sodium gluconate | 93.4 |
| 3 | 33% sodium gluconate, 3 mM metabisulfite | 83.8 |
| 4 | 10% sodium gluconate | 62.2 |
| 5 | 33% sodium gluconate, 2 mM ascorbate, 22 U/ml catalase, 5 mM glucose | 58.0 |
| 6 | 2.4% tetra potassium pyrophosphate and Base A | 57.7 |
| 7 | 500 mM ammonium sulfate and Base A | 55.5 |
| 8 | 2% tetra sodium pyrophosphate and Base A | 50.8 |
| 9 | 9.9% tetra potassium pyrophosphate and Base A | 46.7 |
| 10 | 500 mM ammonium tartrate and Base A | 46.4 |
| 11 | 56 mM dibasic sodium phosphate, 100 mM monobasic potassium phosphate and Base A | 43.2 |
| 12 | 4.8% tetra potassium pyrophosphate and Base A | 41.6 |
| 13 | 28 mM dibasic sodium phosphate, 50 mM monobasic potassium phosphate and Base A | 40.2 |
| 14 | 2% polyethylene glycol 600 and Base A | 38.7 |
| 15 | 20% gluconate and 2.4% tetra potassium pyrophosphate | 37.0 |
| 16 | 2% sodium tripolyphosphate and Base A | 35.8 |
| 17 | 3% polyethylene glycol 6000 and Base A | 35.4 |
| 18 | 40% fructose, 28 mM dibasic sodium phosphate, 50 mM monobasic potassium phosphate and 22 U/ml catalase | 34.9 |
| 19 | 20 mM citrate, 20 mM phosphate pH 6.0 and Base A | 31.3 |
| 20 | 1 mM beta-mercaptoethanol and Base A | 31.2 |
| 21 | 22 U/ml catalase and Base B | 30.1 |
| 22 | 10% sodium gluconate and Base A | 28.9 |
| 23 | 28 mM dibasic sodium phosphate, 154 mM monobasic potassium phosphate and Base A | 28.1 |
| 24 | 40% xylitol, 14 mM dibasic sodium phosphate, 77 mM monobasic potassium phosphate | 27.8 |
| 25 | 1% Tween 20 and Base A | 27.2 |
| 26 | 1 mM ethylenediaminetetraacetic acid and Base A | 27.2 |
| 27 | 14 mM dibasic sodium phosphate, 77 mM monobasic potassium phosphate and Base A | 27.0 |
| 28 | 1 mM ascorbic acid and Base A | 25.2 |
| 29 | 1% sodium dodecylsulfate and Base A | 24.3 |
| 30 | 0.77% metabisulfite and Base B | 23.8 |
| 31 | 2 mM vitamin E, 1% Tween 20 and Base A | 23.2 |
| 32 | 2 mM ascorbate, 22 U/ml catalase and Base B | 22.6 |
| 33 | 40% sorbose, 2 mM ascorbate, 14 mM dibasic sodium phosphate and 77 mM monobasic potassium phosphate | 22.3 |
| 34 | 0.1% polyethylenimine and Base A | 22.3 |
| 35 | 5% sodium gluconate and Base A | 22.0 |
| 36 | 40% sorbitol and 1 mM ascorbic acid | 21.9 |
| 37 | 1% nonidet P-40 and Base A | 21.8 |
| 38 | 0.1% sodium dodecyl sulfate and Base A | 21.5 |
| 39 | 33% gluconate and 2.4% tetra potassium pyrophosphate | 20.3 |
| 40 | Base A | 19.8 |
| 41 | 2 mM D-methionine and Base A | 19.4 |
| 42 | 40% xylitol | 19.3 |
| 43 | 40% sorbitol, 1% Tween, 22 U/ml catalase, 28 mM dibasic sodium phosphate and 50 mM monobasic potassium phosphate | 19.1 |
| 44 | 1% calcium lactate and Base A | 18.6 |
| 45 | 2 mM reduced glutathione and Base A | 16.7 |
| 46 | 2 mM L-cysteine and Base A | 16.6 |
| 47 | 1 mM reduced glutathione, 1 mM oxidized glutathione and Base A | 16.3 |
| 48 | 40% sorbitol, 1% sodium dodecylsulfate, 22 U/ml catalase, 28 mM dibasic sodium phosphate and 50 mM monobasic potassium phosphate | 15.8 |
| 49 | 2 mM ascorbate, 22 U/ml catalase and Base A | 13.3 |
| 50 | 2 mM isoascorbic acid sodium salt and Base A | 12.8 |
| 51 | 20 mM citrate, 20 mM phosphate pH 6.0 | 10.1 |
| 52 | 40% L-sorbose | 7.9 |
| 53 | 40% fructose | 7.0 |
| 54 | 40% propylene glycol | 5.6 |
| 55 | 2 mM ascorbate, 22 U/ml catalase, 5 mM glucose and Base A | 5.5 |
| 56 | 1.9% sodium metabisulfite and Base A | 4.8 |
| 57 | 40% propylene glycol, 1% sodium dodecylsulfate, 2 mM vitamin E | 2.7 |
| 58 | 2 mM ascorbate and Base B | 1.8 |
| 59 | 34% propylene glycol, 20 mM citrate, 20 mM phosphate pH 6.0 | 1.8 |
| 60 | 10% gluconate, 2.4% tetra potassium pyrophosphate | 1.7 |
| 61 | 40% sucrose | 1.7 |
| 62 | 100 mM sorbose and Base A | 1.5 |
| 63 | 40% propylene glycol, 1% 2(3)-t-butyl-4-hydroxyanisole, 2 mM D-Methionine | 1.2 |
| 64 | 40% glycerol | 0.7 |
| 65 | 40% maltose | 0.6 |
| 66 | 40% xylose | 0.4 |
| 67 | 40% sorbitol | 0.2 |
| 68 | 40% sorbitol, 3% glucose | 0.1 |
| 69 | 44% polyethylene glycol 600, 14 mM dibasic sodium phosphate, 77 mM monobasic potassium phosphate | 0.1 |
| 70 | 500 mM ammonium citrate and Base A | 0.04 |
| 71 | 40% sorbitol with 400 mM citrate | 0.002 |
| 72 | Base B | 0.0 |
| 73 | 10% gluconolactone and Base A | 0.0 |

"Base A" contained 18.5% sodium chloride, 1.3% monosodium phosphate, dihydrate, and 2.5% trisodium citrate, dihydrate. "Base B" contained 43% sorbitol, 3% glycerol, 5 g/l sodium chloride and 50 mM monobasic potassium phosphate, adjusted to pH 5.4.

The values of the measured activity of each sample stored at 40° C. at each incubation time were divided by the average of values of measured activity of all the OXYGO® HP L5000 samples stored at 4° C. for the respective incubation time. In this analysis, a value of "1" indicates that there was no loss of activity (i.e., 100% residual activity), while any value below "1" indicates that the sample has lost activity. The values of activity of samples stored at 40° C. relative to samples stored at 4° C. were fitted to a simple exponential decay (Equation 1):

$$\frac{A}{A_o} = e^{-k \times t} \quad (1)$$

In equation 1, "A" represents the activity measured for samples stored at 40° C., "$A_o$" represents the activity measured for a sample stored at 4° C., "k" represents the rate constant that describes the loss of activity, and "t" represents the duration of the incubation time the sample remained at 40° C. FIG. 1, FIG. 2, FIG. 3 and FIG. 4 provide data fit to Equation 1 using non-linear least squares regression analysis, as known in the art.

From all the data collected over the test period, a value of the rate constant, "k," was determined for each sample using Equation 1 and non-linear least squares regression analysis. From the value of the determined rate constant, a percent of remaining activity at 10 weeks was calculated. The percent of remaining activity after 10 weeks of storage at 40° C. for the samples described in Table 1 are presented in FIGS. 5A and 5B These results clearly indicate that sodium gluconate provides excellent storage stability benefit of all of the compositions tested, although metabisulfite and combinations of ascorbate, catalase, glucose, and gluconate, as well as other combinations provided storage stability benefit.

We claim:

1. A composition comprising at least one glucose oxidase, and a storage stability enhancing solution of 18.5% sodium chloride, 1.3% monosodium phosphate dihydrate, 2.5% trisodium citrate dehydrate, and at least one further storage enhancing compound selected from tetra potassium pyrophosphate, ammonium sulfate, ammonium tartrate and tetra sodium pyrophosphate.

2. The composition of claim 1, wherein said composition retains at least about 15% of its initial activity after about 10 weeks of storage at about 40° C.

3. The composition of claim 1, wherein said composition retains at least about 30% of its initial activity after about 10 weeks of storage at about 40° C.

4. The composition of claim 1, wherein said composition is retains at least about 50% of its initial activity after about 10 weeks of storage at about 40° C.

5. The composition of claim 1, wherein said composition retains at least about 70% of its initial activity after about 10 weeks of storage at about 40° C.

6. The composition of claim 1, wherein said composition is a personal care composition.

7. The composition of claim 1, wherein said composition is stable after storage at a pH range of about 5.0 to about 7.

8. The composition of claim 1, wherein said composition is stable after storage at about pH 7.

9. The composition of claim 1, wherein said composition is stable after storage at a temperature ranging from about 4° C. to about 50° C.

10. The composition of claim 1, wherein said composition is stable after storage at a temperature ranging from less than about 4° C. to about 40° C.

11. A method for stabilizing glucose oxidase in a composition comprising:
   a) providing glucose oxidase and a stability enhancing solution of 18.5% sodium chloride, 1.3% monosodium phosphate, dihydrate, and 2.5% trisodium citrate, dihydrate, and at least one storage stability enhancing compound selected from tetra potassium pyrophosphate, ammonium sulfate, ammonium tartrate, and tetra sodium pyrophosphate; and
   b) combining said glucose oxidase and said at least one stability enhancing compound to produce a stabilized glucose oxidase composition.

12. The method of claim 11, wherein said composition is stable for about 10 weeks at about 40° C.

13. The method of claim 11, wherein said composition is a personal care composition.

* * * * *